(12) United States Patent
Lampkins

(10) Patent No.: US 6,328,707 B1
(45) Date of Patent: *Dec. 11, 2001

(54) ANKLE RESTRAINING DEVICE

(76) Inventor: Gary W. Lampkins, 2130 Brooks. Dr., Forestville, MD (US) 20747

( * ) Notice: Subject to any disclaimer, the term of this patent is extended or adjusted under 35 U.S.C. 154(b) by 0 days.

This patent is subject to a terminal disclaimer.

(21) Appl. No.: 08/221,381

(22) Filed: Mar. 29, 1994

(51) Int. Cl.$^7$ .................................................. A61F 5/00
(52) U.S. Cl. .............................. 602/23; 602/27; 128/882
(58) Field of Search ............................... 602/4, 5, 23, 24, 602/25, 26, 27, 28, 60, 62, 64, 65; 128/882, 869

(56) References Cited

U.S. PATENT DOCUMENTS

| | | | |
|---|---|---|---|
| 453,475 | * 6/1891 | Harding | 602/27 |
| 1,114,389 | * 10/1914 | Semeleder | 602/27 |
| 1,585,828 | * 5/1926 | Bierig | 602/29 |
| 2,531,486 | * 11/1950 | Weber | 602/28 |
| 2,871,852 | * 3/1959 | Miller | 602/24 |
| 3,805,773 | * 4/1974 | Sichau | 602/28 |
| 4,691,698 | * 9/1987 | Bremer | 602/24 |
| 4,969,452 | * 11/1990 | Petrofsky | 602/27 |

* cited by examiner

Primary Examiner—Michael A. Brown

(57) ABSTRACT

An orthopedic athletic shoe that will prevent the ankle from twisting to an injurious position while allowing full range of motion of the foot and ankle. Said shoe will consist of a means to secure around the lower leg with a housing with a hole at the top attached thereto. The housing will enclose a disk that is sizably smaller than the housing to allow the disk to move in all directions. The disk will attach to a joint thru the hole of the housing and an arm extention will attach to said joint and extend down towards the ankle at which a second joint adjacent to the middle of the ankle will attach to the other end of said arm extention. Said second joint also has an arm extention that proceeds down to the foot and attaches to a third joint that is connected to a disk that is smaller than the housing upon which it is enclosed with the housing being securely fasten to the side of the foot area of the shoe.

13 Claims, 8 Drawing Sheets

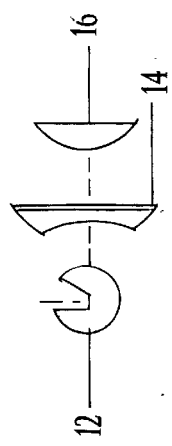
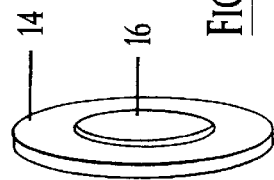
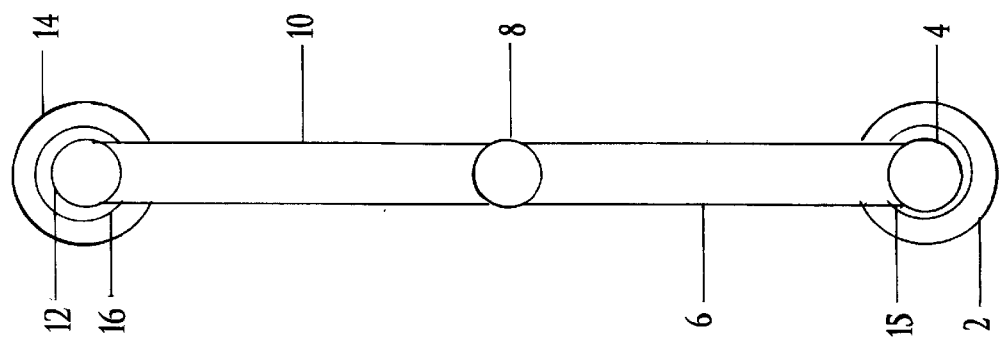

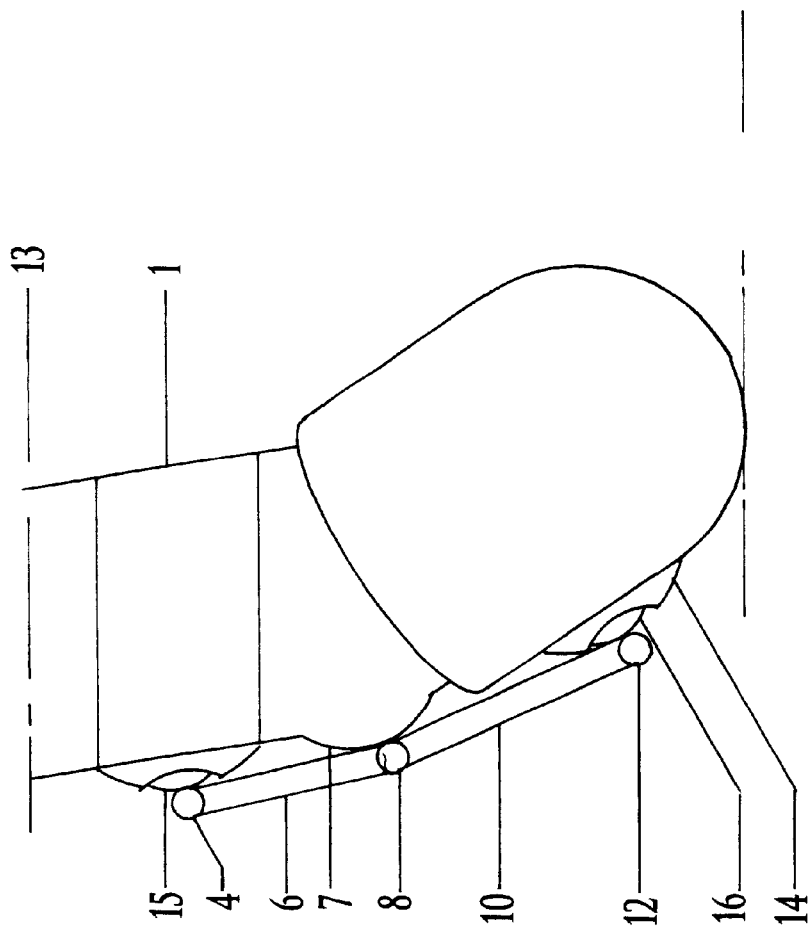

ANKLE RESTRAINING DEVICE

BACKGROUND OF THE INVENTION

This invention will allow a person engaging in any athletic activity, to function normally and uninhibited by its presence, yet when a twist occurs provide the support necessary to keep the ankle from injury.

Background information on an orthopedic shoe or device attached thereto is contained in Sichau U.S. Pat. No. 3,805,773 a device that provides support to the leg and foot of a patient that is experiencing difficulty during walking. Also reference is made in Harding U.S. Pat. No. 453,475 an orthopedic shoe that claimed to be less painful and more efficient to a person with deformed feet. Moreover, Semeleder U.S. Pat. No. 1,114,389 an apparatus for correcting foot crookednesses provides background information that most closely effects the invention heretofore made.

SUMMMARY OF THE INVENTION

The purpose of this invention is to provide an orthopedic athletic shoe that will preclude the athlete from twisting the ankle to an injurious position while competing in activities that require speed, agility and flexibility. This will be accomplished by a leg strapping means attached to the lower leg right above the ankle, a housing that has a hole at the top of it with a disk enclosed attached to said leg strapping member, a joint attaching to said disk on one end and an arm extention on the other which in turn, attaches to another joint located adjacent to the middle of the ankle. A second arm extention will attach to said joint adjacent to the ankle and extend down to the foot where it attaches to a third joint which attaches to a disk enclosed in a housing that is attached to the foot. The disk within the housing is smaller than the housing to allow said disk to move freely within the housing, and consequently allow the foot and ankle to move freely uninhibited by the apparatus. However, if a twisting or turning of the ankle occurs said shoe would restrain the ankle and foot and keep the athlete from injury.

BRIEF DESCRIPTION OF THE DRAWINGS

FIG. 3 is a side view of the invention that illustrates the three joints and two arm extentions and how they are align with the disks being enclosed in the housings.

FIG. 4 is an open end view of the housing and the disk that allows the movements described.

FIG. 5 is a illustration of the joint the housing and the disk.

FIG. 12 is a rear view of the invention incorporating FIG. 11 illustrating the flexing capabilities.

DESCRIPTION OF THE PREFERRED EMBODIMENTS

Figure 1:
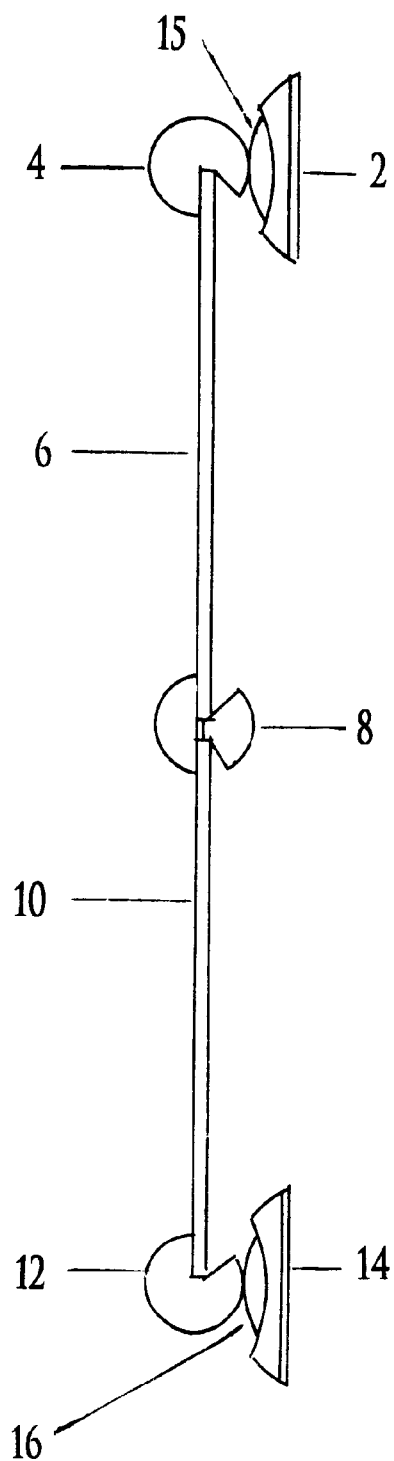
FIG. 1 is a rear view of the invention.
Figure 2:
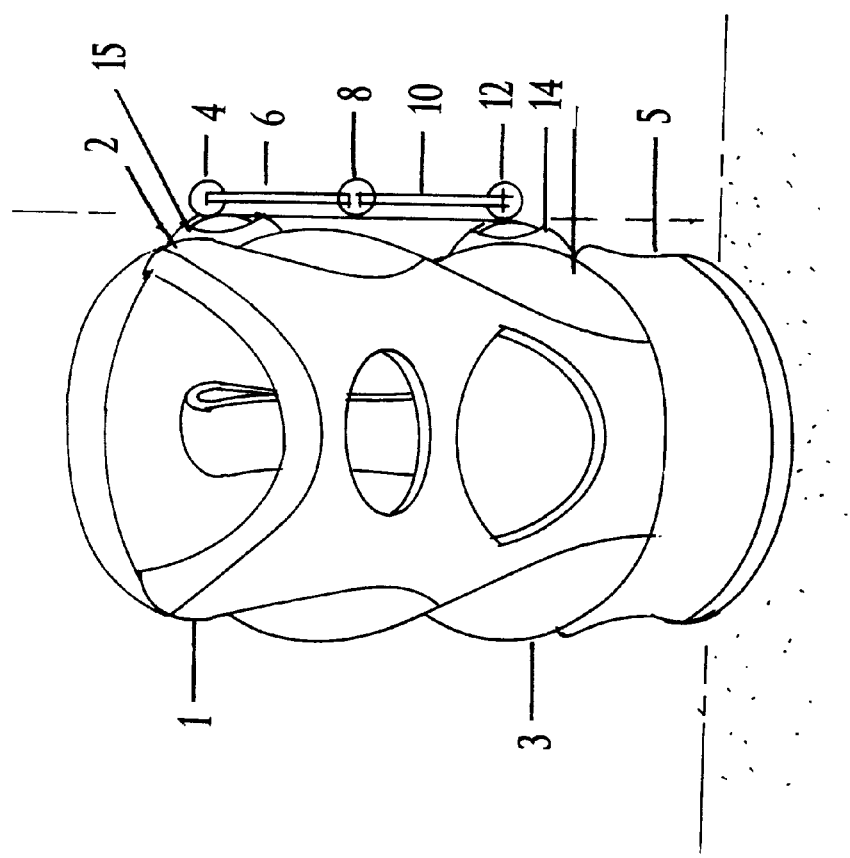
FIG. 2 is a rear view of the invention illustrating its primary function which is to reinforce the ankle and foot.

The illustration in FIG. 1 shows a rear view of the lower leg 13, a leg strap 1, an ankle 7 and a foot within a shoe 3 with an attachment device being attached to the leg strap 1 on one end and the outer heel area of the shoe 3 on the other. The leg strap 1 is secured around the lower leg 13 with a first housing 2 in the shape of a dome with a hole 18 at the top of it attached to its outer portion. The Leg strap 1 and a first housing 2 attached thereto serves as the anchor to the upper portion of the attachment device. There is a first disc 15 within the first housing 2 that attaches to the first joint 4 thru a hole 18 of the first housing 2. An arm extention 6 also attaches to the first joint 4. The purpose of the first joint 4 is to allow normal flexion of the ankle and the foot. The Arm extentions 6 main functions are to connect the first joint 4 with the second joint 8 and provide stability and strength to the attachment device. As illustrated in FIG. 1 a second joint 8 is located adjacent to the ankle 7 and serves as the connecting point for arm extention 6 and another arm extention 10. The arm extention 10 will also connect to a third joint 12 which is attached to a second disc 16 within a second housing 14 thru a hole 17 of the second housing 14, with the second housing 14 being securely fastened to the outer heel area of the shoe 3 right above the sole 5. A Second housing 14 is also in the shape of a dome as was the first housing 2. As illustrated in FIG. 2 the ankle 7 twisting or rolling outward will be restrained by the attachment device. This is acheived by the leg strap 1 and the first housing 2 attached thereto, being securely strapped around the lower leg 13, with a first disc 15 being within the first housing 2, with the arm extention 6 attached to the first joint 4, with a second joint 8 also attached to the arm extention 6, with the second joint 8 also attached to another arm extention 10, which is attached to a third joint 12, with the third joint 12 attached to a second disc 16 thru a hole 17 of the second housing 14, with the second housing 14 being securely fastened to the outer heel area of the shoe 3 right above the sole 5, with all of the above named components functioning as one unit to restrain the ankle 7 and the foot within the shoe 3, which, will ultimately, protect the athlete from injury.

A side view of the attachment device unattached to the shoe 3 is displayed in FIG. 3. It shows the first housing 2 with the hole 18 at the top of it, with the first disc 15 therein. The first disc 15 is sizably smaller than the first housing 2 to allow the first disc 15 freedom of movement in all directions within the first housing 2. This will allow full range of motion of the ankle 7 and foot. Also it shows the first joint 4 attached to the first disc 15 thru the hole 18 of the first housing 2, with the hole 18 being smaller than the first disc 15 to keep the first disc 15 within the parameters of the first housing 2. The first joint 4 will also attach to the arm extention 6 which is attached to the second joint 8, which is attached to the arm extention 10, which is attached to the third joint 12 ,which is attached to the second disc 16 thru the hole 17 of the second housing 14 upon which the second disc 16 is enclosed. Moreover, the second disc 16 is sizably smaller than the second housing 14 to allow the second disc 16 freedom of movement in all directions within the second housind 14 , yet, the second disc 16 is larger than the hole 17 of the second housing 14 to keep the second disc 16 within the parameters of the second housing 14.

FIG. 4 illustrates a back view of the first housing 2 with the first disc 15 therein, with the first joint 4 attached to the first disc 15. This angle shows that the first disc 15 is smaller than the first housing 2 to allow the first disc 15 freedom of movement within the parameters of the first housing 2.

FIG. 5 illustrates an exploded side view of the third joint 12, with the hole 17 of the second housing 14 and a second disc 16. This illustration shows the difference in the size of the components.

Figure 6:
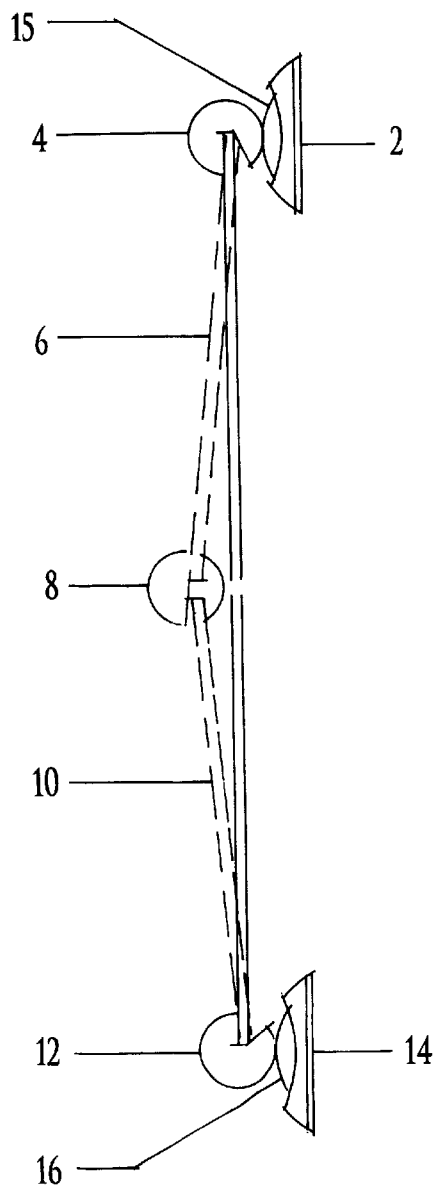
FIG. 6 is a rear view of the invention unattached to the shoe illustrating its flexing capabilities.
Figure 7:
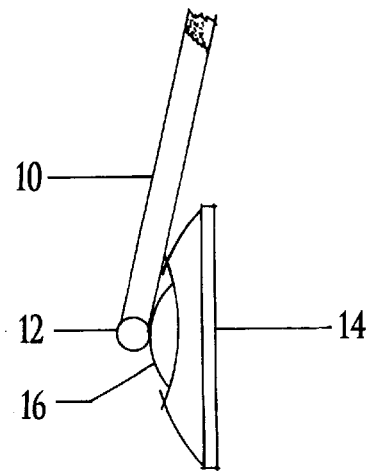
FIG. 7 is a rear view of the invention unattached to a shoe showing extreme flexibility of the bottom joint.

FIGS. 6 and 7 illustrate the flexing capabilities of the first, the second, and the third joints 4, 8, and 12 joined together by the arm extentions 6 and 10, with the first joint 4 being attached to the first disc 15 thru the hole 18 of the first housing 2, and, the third joint 12 being attached to the second disc 16 thru the hole 17 of the second housing 14. Also FIG. 7 shows the positions of the components when the attachment device flexes.

Figure 8:
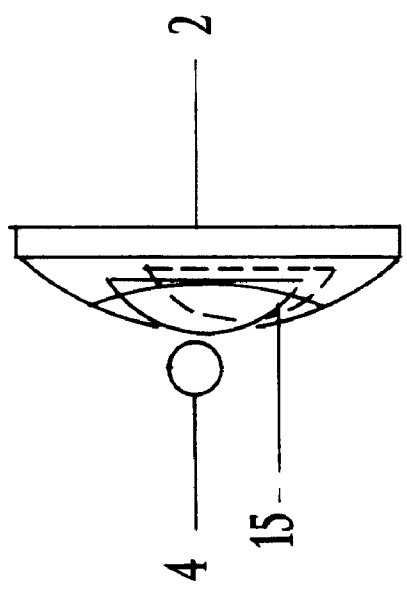
FIG. 8 is a side view of a joint, housing,and disk with the movements of the disk in phantom.

FIG. 8 illustrates the first joint 4 attached to the first disc 15 thru the hole 18 of the first housing 2, with a movement of the disc 15 in phathom.

Figure 9:
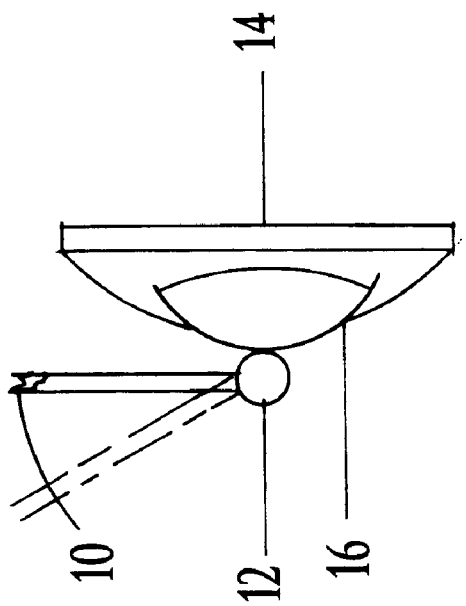
FIG. 9 is a side view of the bottom joint, the housing and the arm extention and its flexing in phantom.

FIG. 9 illustrates an inward movement of the arm extention 10 attached to the third joint 12 as it relates to the second housing 14.

Figure 10:
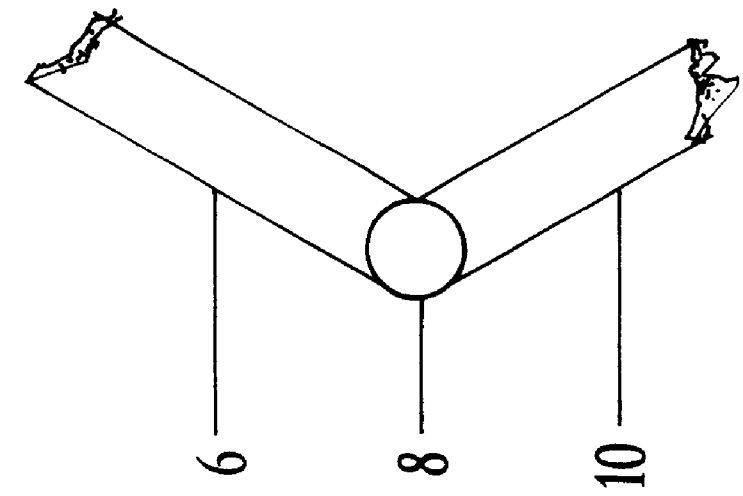
FIG. 10 is a side view of the two arm extentions attached to the middle joint with an arm extention flexing inward to form an obtuse angle.

FIG. 10 illustrate the arm extentions 6 and 10 attached to the second joint 8 with the arm extention 6 flexing inward in phathom to display a movement capability.

Figure 11:
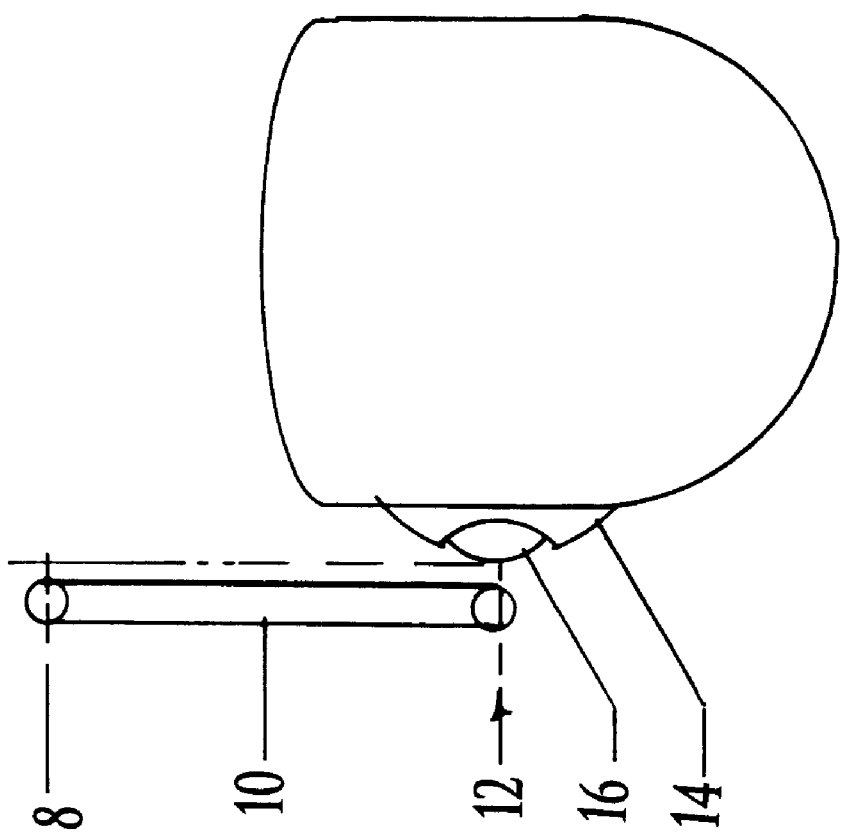
FIG. 11 is a rear view of the invention attached to a heel cup with the middle joint being a hinge with a safety catch attached thereto.

FIGS. 11 and 12 are illustrations of a leg strap, a rotary ball attached to the leg strapping means, with an arm extention attached to the rotary ball. The arm extention is also attached to a hinge located adjacent to the ankle, with a second arn extention attached to the other wing of the hinge, with the second arm extention attached to the heel cup of a shoe. FIG. 12 illustrates the flexion of the hinge and the positions of the components when the hinge flexes.

Figure 13:
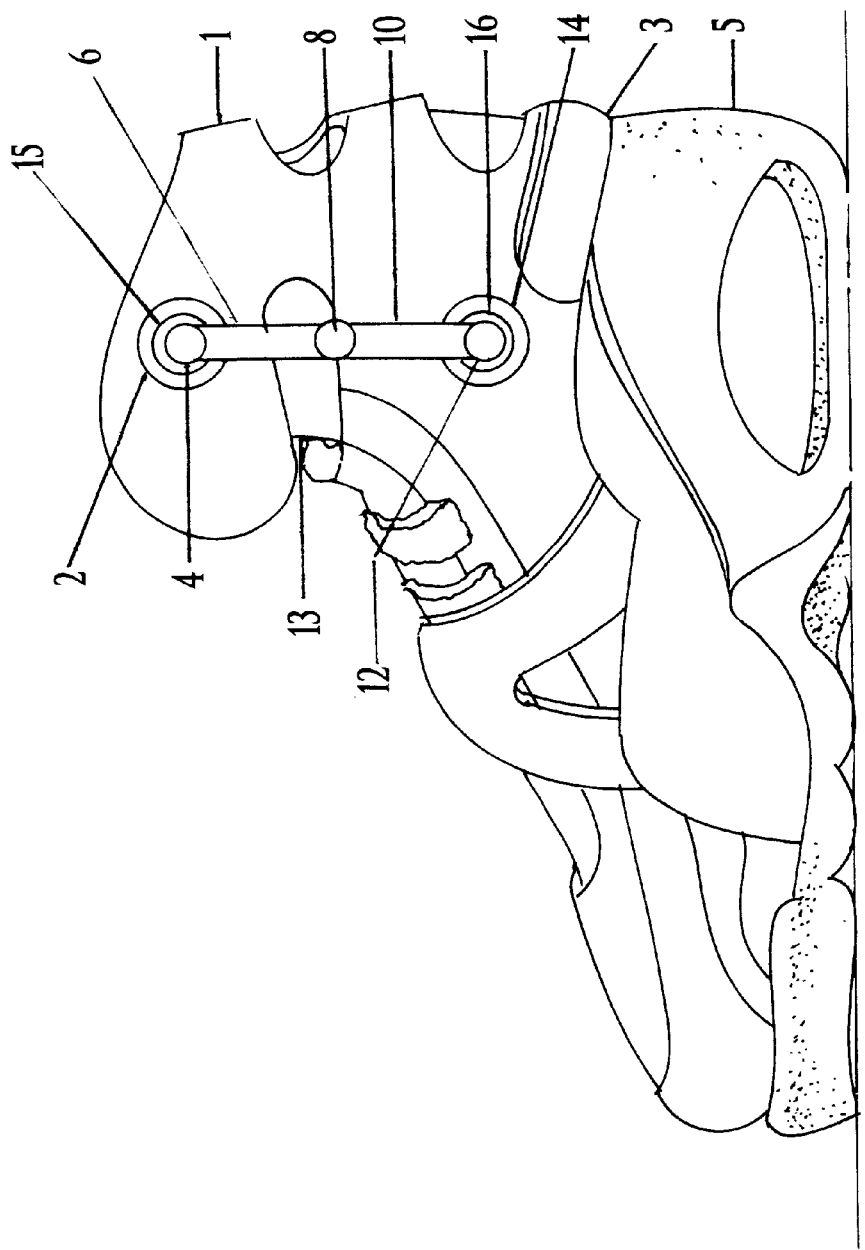
FIG. 13 is a side view of the invention, an orthopedic athlete shoe.

FIG. 13 illustrates a side view of a shoe 3 with a leg strap 1 attached thereto and made a part of the shoe 3, with the first, the second, and the third joints 4, 8, and 12 joined together by the arm extentions 6 and 10, with the arm extention 6 connecting to the first joint 4, which thru the hole 18 of the first housing 2, will attach to the first disc 15 which is within the first housing 2, with the first housing 2 being attached to the leg strap 1. It further displays, the second housing 14 with the second disc 16 therein, with the second housing 14 attached to the outer heel area of the shoe 3 right above the sole 5, with the third joint 12 attached to the second disc 16 thru the hole 17 of the second housing 14.

I claim:

1. An orthopedic athletic shoe that prevents the ankle from twisting to an injurious position while allowing full range of motion of the ankle and foot, comprising a sole, a shoe, a lower leg member adapted to be secured to a lower leg, an attachment means extending from said shoe to said lower leg member, said attachment means having a first and second ends, said first end is attached to a first disc which is located in a first housing, a second housing, said second housing is attached to said second end of said attachment means and said shoe, a first joint, said first disc is attached to said attachment means by said joint, wherein said orthopedic shoe prevents an ankle from twisting when the user lands off balance.

2. The orthopedic athletic shoe of claim 1, wherein said second housing has a hole therein, wherein said hole is smaller than said disc.

3. The orthopedic athletic shoe of claim 1, wherein said second housing has a second disc therein.

4. The orthopedic athletic shoe of claim 1, wherein said first housing has a hole therein.

5. The orthopedic athletic shoe of claim 1, wherein said hole in said first housing is smaller than said first disc.

6. The orthopedic athletic shoe of claim 1, wherein said attachment means has a second and a third joint.

7. The orthopedic athletic shoe of claim 1, wherein said third joint attaches said second disc to said attachment means.

8. The orthopedic athletic shoe of claim 1, wherein said first disc is smaller than said first housing.

9. The orthopedic athletic shoe of claim 1, wherein said second disc is smaller than said second housing.

10. The orthopedic athletic shoe of claim 1, wherein said attachment means is a strap.

11. The orthopedic athletic shoe of claim 1, wherein said lower leg member is attached to and made a part of said athletic shoe.

12. The orthopedic athletic shoe of claim 1, wherein said attachment means has a hinge.

13. The orthopedic athletic shoe of claim 1, wherein said attachment means has a rotary ball.

* * * * *